(12) United States Patent
Jukes et al.

(10) Patent No.: US 8,821,579 B2
(45) Date of Patent: Sep. 2, 2014

(54) TIBIAL COMPONENT WITH FLEXIBLE RIM

(75) Inventors: Andrew J. Jukes, Wetzikon (CH);
Rosemary E. Thompson, Elgg (CH);
Jörg Zimmermann, Winterthur (CH)

(73) Assignee: Zimmer GmbH, Winterthur (CH)

(*) Notice: Subject to any disclaimer, the term of this patent is extended or adjusted under 35 U.S.C. 154(b) by 108 days.

(21) Appl. No.: 12/868,095

(22) Filed: Aug. 25, 2010

(65) Prior Publication Data

US 2011/0098823 A1  Apr. 28, 2011

Related U.S. Application Data

(60) Provisional application No. 61/236,986, filed on Aug. 26, 2009.

(51) Int. Cl.
*A61F 2/38* (2006.01)

(52) U.S. Cl.
USPC ...................................... 623/20.32

(58) Field of Classification Search
USPC .......... 623/20.14, 20.15, 20.21, 20.22, 20.24, 623/20.25, 20.26, 20.28, 20.29, 20.3, 20.31, 623/20.32, 20.33, 21.15–21.19, 23.42
See application file for complete search history.

(56) References Cited

U.S. PATENT DOCUMENTS

| | | | |
|---|---|---|---|
| 4,673,407 A * | 6/1987 | Martin | 623/20.33 |
| 5,074,880 A | 12/1991 | Mansat | |
| 5,509,934 A | 4/1996 | Cohen | |
| 5,609,643 A * | 3/1997 | Colleran et al. | 623/20.29 |
| 5,824,104 A | 10/1998 | Tuke | |
| 5,879,394 A | 3/1999 | Ashby et al. | |
| 6,258,126 B1 * | 7/2001 | Colleran | 623/20.29 |
| 6,379,388 B1 | 4/2002 | Ensign et al. | |
| 6,569,202 B2 | 5/2003 | Whiteside | |
| 2005/0015153 A1 * | 1/2005 | Goble et al. | 623/23.46 |
| 2005/0055101 A1 * | 3/2005 | Sifneos | 623/20.32 |
| 2005/0246027 A1 * | 11/2005 | Metzger et al. | 623/20.15 |
| 2006/0224244 A1 | 10/2006 | Thomas et al. | |
| 2008/0154369 A1 * | 6/2008 | Barr et al. | 623/11.11 |
| 2008/0195216 A1 | 8/2008 | Philipp | |
| 2009/0228112 A1 | 9/2009 | Clark et al. | |

* cited by examiner

*Primary Examiner* — Marcia Hoffman
(74) *Attorney, Agent, or Firm* — Schwegman Lundberg & Woessner, P.A.

(57) ABSTRACT

A tibial prosthesis including an articulating component and a tray component with a rim that extends proximally to support the articulating component, the tray component enabling flexion of the rim relative to a bone-contacting surface of the tray component.

21 Claims, 3 Drawing Sheets

TIBIAL COMPONENT WITH FLEXIBLE RIM

CROSS REFERENCE TO RELATED APPLICATION

This application claims priority from U.S. Provisional Patent Application Ser. No. 61/236,986, entitled "TIBIAL COMPONENT WITH FLEXIBLE RIM," filed Aug. 26, 2009, the disclosure of which is hereby expressly incorporated by reference herein in its entirety.

BACKGROUND

1. Field of the Invention

The present invention relates to the field of orthopedics. More particularly, the present invention relates to a tibial prosthesis, and to a method for using the same.

2. Description of the Related Art

Orthopedic prostheses are commonly used to repair and replace damaged bone and tissue in the human body. For example, to repair damaged bone of the knee joint and to recreate the natural, anatomical articulation of the knee joint, a tibial prosthesis may be implanted in the proximal tibia and/or a femoral prosthesis may be implanted in the distal femur.

The tibial prosthesis may include a first, articulating component having a concave articulating surface configured for articulation against a natural femur or a femoral prosthesis. The tibial prosthesis may also include a second, tray component having a bone-contacting surface configured for securing the tibial prosthesis to the bone stock of a resected proximal tibia. The articulating component may be made from a polymer to facilitate articulation with the adjacent femoral prosthesis, while the tray component may be made from a metal to provide additional strength and rigidity to the tibial prosthesis.

SUMMARY

The present invention provides a tibial prosthesis a tibial prosthesis including an articulating component and a tray component with a lip that extends proximally to support the articulating component, the tray component enabling flexion of the lip relative to a bone-contacting surface of the tray component.

According to an embodiment of the present invention, a tibial prosthesis is provided that is configured for securement to a patient's tibia and for articulation with an adjacent femoral component. The tibial prosthesis includes an articulating component and a tray component. The articulating component includes a concave articulating surface to facilitate articulation with the femoral component. The tray component includes a proximal, receiving surface that receives the articulating component, a distal, bone-contacting surface opposite the receiving surface that is configured for securement to the patient's tibia, and an outer surface that extends proximally from the bone-contacting surface and beyond the receiving surface to define a rim for supporting the articulating component, the outer surface of the tray component defining a notch positioned to permit flexion of the rim relative to the bone-contacting surface of the tray component.

According to another embodiment of the present invention, a tibial prosthesis is provided that is configured for securement to a patient's tibia and for articulation with an adjacent femoral component. The tibial prosthesis includes an articulating component and a tray component. The articulating component has a concave articulating surface to facilitate articulation with the femoral component. The tray component has a proximal, receiving surface that receives the articulating component and a distal, bone-contacting surface opposite the receiving surface that is configured for securement to the patient's tibia, the tray component including a rim that extends proximally beyond the receiving surface to support the articulating component, the rim defining a notch that extends into the rim until reaching an inflection point, the inflection point located along an arcuate surface of the rim to permit flexion of the rim relative to the bone-contacting surface of the tray component at the inflection point.

According to yet another embodiment of the present invention, a method is provided for implanting a tibial prosthesis onto a patient's tibia. The method includes the steps of: providing the tibial prosthesis including an articulating component and a tray component, the tray component having a proximal, receiving surface that receives the articulating component, a bone-contacting surface, and a peripheral rim that supports the articulating component, the peripheral rim having an inner surface that faces the articulating component and an outer surface that defines a notch; and securing the tibial prosthesis to the patient's tibia with the bone-contacting surface of the tibial prosthesis facing the patient's tibia, the notch permitting flexion of the rim relative to the patient's tibia.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
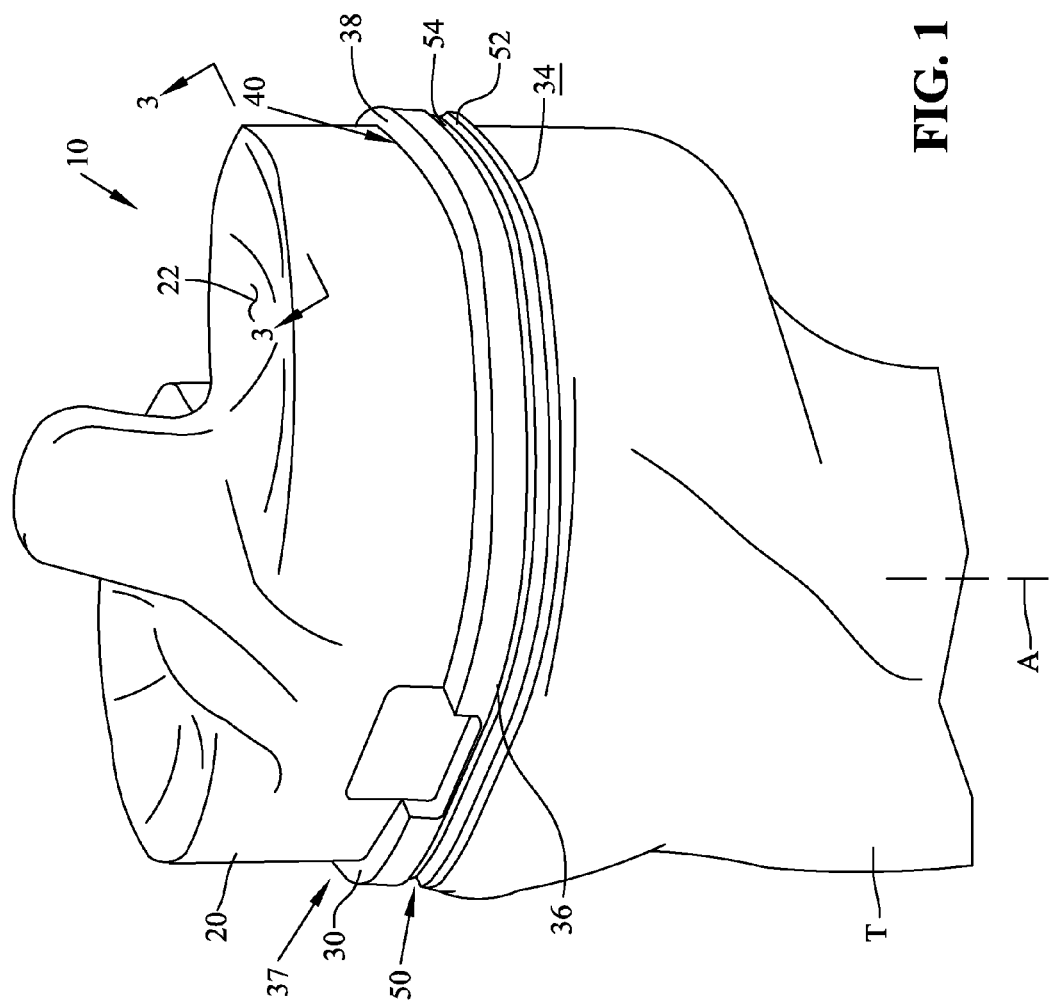
FIG. 1 is a proximal perspective view of an exemplary tibial prosthesis of the present invention implanted in a resected proximal tibia, the tibial prosthesis including a first, articulating component mounted atop a second, tray component.

Referring to FIG. 1, an exemplary tibial prosthesis 10 is shown implanted onto a resected proximal tibia T. Tibial prosthesis 10 includes a first, articulating component 20 mounted atop a second, tray component 30. Tibia T includes a longitudinal axis A.

As shown in FIG. 1, articulating component 20 of tibial prosthesis 10 includes at least one concave articulating surface 22 configured for articulation against a natural femur (not shown) or a femoral prosthesis (not shown). To facilitate articulation with an adjacent femoral component, articulating component 20 of tibial prosthesis 10 may be constructed of a smooth, abrasion-resistant material. Also, to provide cushioning to the knee joint, articulating component 20 of tibial prosthesis 10 may be constructed of a resilient, deformable material. For example, articulating component 20 may be constructed of a biocompatible polymer, including, but not limited to, a hydrogel, poly ether ether ketone, fiber reinforced poly ether ether ketone, ultrahigh molecular weight polyethylene, crosslinked ultrahigh molecular weight polyethylene, or polyether ketone ether ether ketone. It is also within the scope of the present invention that articulating component 20 may be constructed of a more rigid material like a biocompatible ceramic. Suitable ceramics include oxide ceramics, such as alumina or zirconia, and non-oxide ceramics, such as silicon nitride or silicon carbide.

Figure 2:
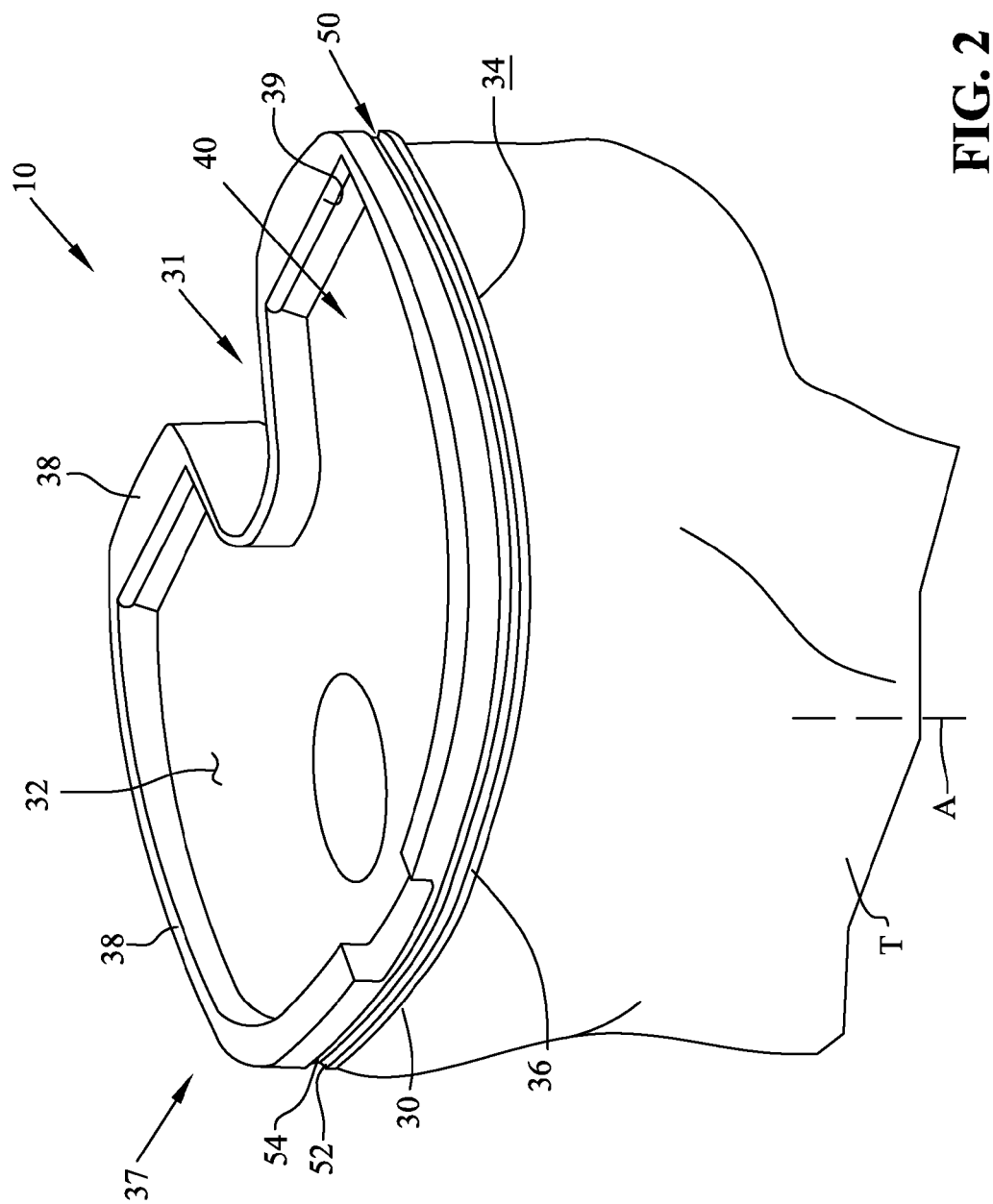
FIG. 2 is a proximal perspective view similar to FIG. 1 of the tray component implanted in the resected proximal tibia, the tibial prosthesis shown without the articulating component mounted atop the tray component.
Figure 3:
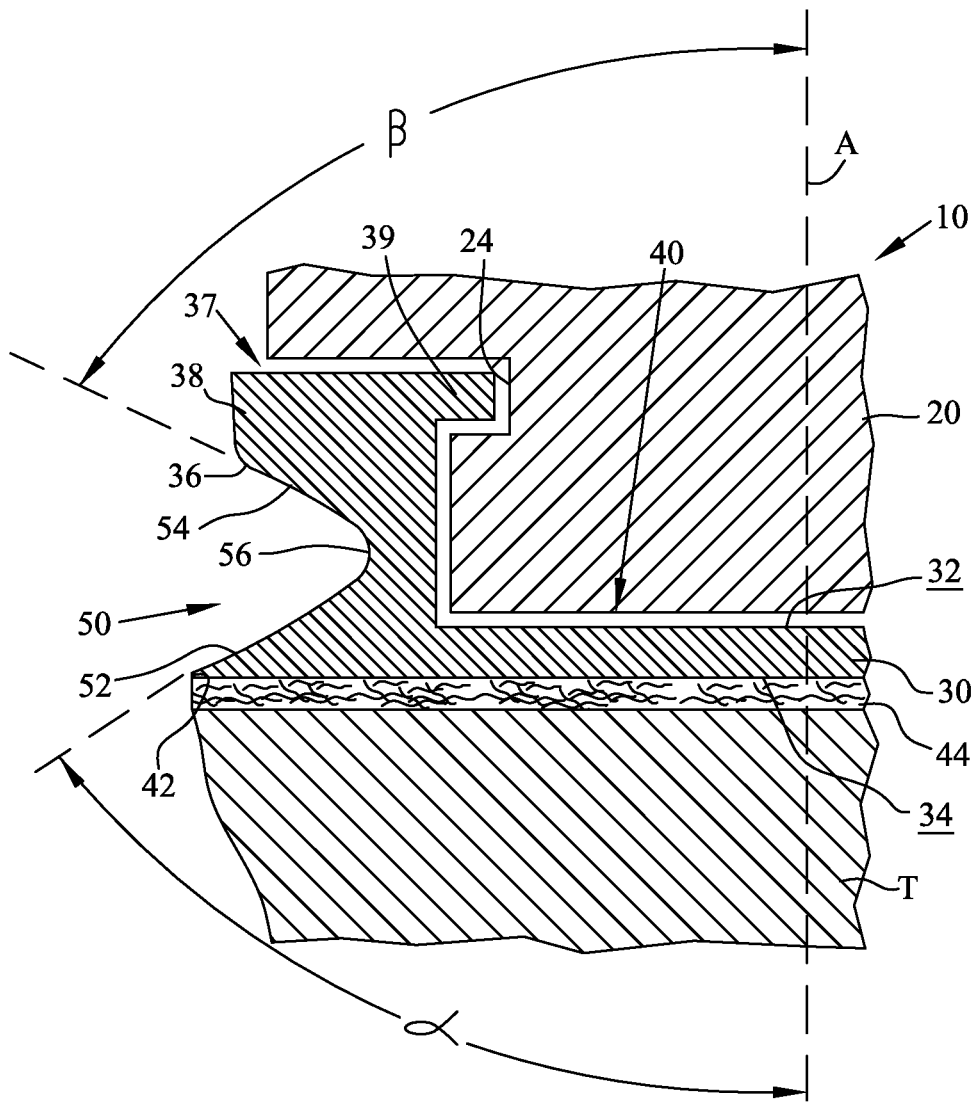
FIG. 3 is a cross-sectional view of the tibial prosthesis and the resected proximal tibia of FIG. 1, taken along line 3-3 of FIG. 1.

Referring next to FIGS. 2 and 3, tray component 30 of tibial prosthesis 10 is substantially U-shaped with posterior recess 31 being sized and shaped to receive the patient's posterior cruciate ligament (PCL). Tray component 30 of tibial prosthesis 10 includes a substantially planar, proximal receiving surface 32 and a substantially planar, distal bone-contacting surface 34 located opposite receiving surface 32. Tray component 30 of tibial prosthesis 10 also includes peripheral wall 36 that extends between receiving surface 32 and bone-contacting surface 34. As shown in FIG. 3, bone-contacting surface 34 of tray component 30 includes outer edge 42 that borders peripheral wall 36.

To provide strength and rigidity to tibial prosthesis 10, tray component 30 may be constructed of a rigid biocompatible ceramic or metal. For example, tray component 30 may be constructed of titanium, a titanium alloy, a zirconium alloy, tantalum, cobalt chromium, cobalt chromium molybdenum, porous tantalum, or a highly porous biomaterial. A highly porous biomaterial is useful as a bone substitute and as cell and tissue receptive material. An example of such a material is produced using Trabecular Metal™ technology generally available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861, the disclosure of which is expressly incorporated herein by reference.

As shown in FIG. 2, receiving surface 32 of tray component 30 is configured to receive and mate with articulating component 20 (FIG. 1). Peripheral wall 36 of tray component 30 extends proximally beyond receiving surface 32 to define an outer rim or lip 38. Receiving surface 32 and rim 38 of tray component 30 cooperate to define chamber 40. According to an exemplary embodiment of the present invention, when articulating component 20 is received within chamber 40 of tray component 30, as shown in FIG. 1, articulating component 20 rests against receiving surface 32 of tray component 30 and is supported externally by rim 38 of tray component 30.

Articulating component 20 may be attached to tray component 30 via an interference fit, with a mechanical fastener, or with an adhesive, for example. Also, some or all portions of rim 38 may include flange 39 that projects inwardly into chamber 40. In this embodiment, and as shown in FIG. 3, articulating component 20 may include groove 24 that is sized to receive flange 39 of rim 38 in a tongue and groove arrangement to prevent articulating component 20 from lifting off of tray component 30.

Bone-contacting surface 34 of tray component 30 is configured for attachment to the bone stock of a resected proximal tibia T. An exemplary attachment method involves using a layer of adhesive 44, such as bone cement, which may not only provide a secure connection between tray component 30 and tibia T, but may also strengthen tibia T. Adhesive layer 44 may include any known medical grade adhesive having sufficient strength to secure tray component 30 to tibia T, including, but not limited to, light curable acrylic adhesives, acrylic adhesives, cyanoacrylate adhesives, silicone adhesives, urethane adhesives, epoxy adhesives, and bone cement.

To stabilize tray component 30 and to prevent rotation of tray component 30, tray component 30 may include at least one anchor (not shown), such as a stem or a keel, that extends distally from bone-contacting surface 34 and into the intramedullary canal of tibia T. The intramedullary canal of tibia T may be filled with adhesive to hold the anchor in place. Also, tray component 30 may include pockets (not shown) recessed into bone-contacting surface 34 for receiving adhesive layer 44 between tray component 30 and tibia T.

According to an exemplary embodiment of the present invention, rim 38 of tray component 30 includes notch 50. As shown in FIG. 3, notch 50 extends radially inwardly into peripheral wall 36 to narrow tray component 30 along notch 50. In an exemplary embodiment, notch 50 extends inwardly through a majority of the width of rim 38. Notch 50 may extend entirely or substantially entirely about peripheral wall 36 of tray component 30. Notch 50 may extend into peripheral wall 36 of tray component 30 proximally beyond receiving surface 32, such that notch 50 extends into rim 38 of tray component 30. Also, notch 50 may extend into peripheral wall 36 of tray component 30 between receiving surface 32 and bone-contacting surface 34, such that notch 50 extends beneath rim 38 of tray component 30. In an exemplary embodiment, notch 50 spans a majority of the height of tray component 30. In use, notch 50 of tray component 30 may remain open and unfilled.

In the illustrated embodiment of FIG. 3, notch 50 is bordered distally by first chamfered portion 52 of peripheral wall 36 and is bordered proximally by second chamfered portion 54 of peripheral wall 36. Between first chamfered portion 52 and second chamfered portion 54, peripheral wall 36 includes an inner-most inflection point 56. According to an exemplary embodiment of the present invention, peripheral wall 36 is arcuate in shape along inflection point 56. It is within the scope of the present invention that first chamfered portion 52 and second chamfered portion 54 of peripheral wall 36 may be linear or arcuate in shape.

With bone-contacting surface 34 of tray component 30 seated against the resected proximal tibia T, first chamfered portion 52 of peripheral wall 36 extends inwardly toward longitudinal axis A at first acute angle α, and second chamfered portion 54 of peripheral wall 36 extends inwardly toward longitudinal axis A at second acute angle β. First acute angle α and second acute angle β may equal approximately 20°, 30°, 40°, 50°, 60°, or 70°, for example. First acute angle α and second acute angle β may be substantially the same, or first acute angle α may differ from second acute angle β.

As shown in FIG. 3, first chamfer portion 52 of peripheral wall 36 terminates distally upon reaching outer edge 42 of bone-contacting surface 34. However, it is within the scope of the present invention that first chamfer portion 52 of peripheral wall 36 may terminate distally before reaching outer edge 42 of bone-contacting surface 34, with peripheral wall 36 continuing distally in a vertical direction to meet outer edge 42 of bone-contacting surface 34. Also, second chamfer portion 54 of peripheral wall 36 is shown terminating proximally before reaching top end 37 of rim 38, with peripheral wall 36 continuing proximally in a vertical direction to meet top end 37 of rim 38. However, it is within the scope of the present invention that second chamfer portion 54 of peripheral wall 36 may terminate proximally upon reaching top end 37 of rim 38.

By providing notch 50, tray component 30 may be constructed of less material than a solid tray component 30 lacking notch 50. Advantageously, this material reduction may be achieved without reducing the surface area of receiving surface 32, the surface area of bone-contacting surface 34, the thickness of tray component 30 from receiving surface 32 to bone-contacting surface 34, and/or the height of rim 38. For example, as shown in FIG. 3, the location of notch 50 does not interfere with the surface area of bone-contacting surface 34, so outer edge 42 of bone-contacting surface 34 defines an outer-most perimeter of tray component 30 that fully spans across the patient's tibia T.

As a result of this material reduction, tray component 30 may be more flexible along notch 50 than a solid tray component 30 lacking notch 50, such that tray component 30 is able to bend or flex along notch 50. For example, rim 38 of tray component 30 may be able to bend or flex along notch 50 relative to bone-contacting surface 34 of tray component 30. By providing notch 50 with an arcuate peripheral wall 36 along inflection point 56, flexion may be encouraged at inflection point 56 while limiting stress concentrations at inflection point 56. Advantageously, this flexibility may be achieved without altering the rigidity of tray component 30 itself. For example, tray component 30 may still be constructed of a rigid metal such as titanium, a titanium alloy, a zirconium alloy, tantalum, cobalt chromium, or cobalt chromium molybdenum to provide strength and rigidity to tibial prosthesis 10 while achieving flexibility along notch 50.

The present inventors have recognized that traction forces and pulsing forces on tibial prosthesis 10 reach a maximum level along peripheral wall 36 and rim 38 of tray component 30. Due to these high forces along peripheral wall 36 and rim 38 of tray component 30, the present inventors have observed from X-rays that implanted tray components 30 begin detaching from the bone stock of tibia T and adhesive layer 44 along the adjacent outer edge 42 of bone-contacting surface 34. By providing tray component 30 having notch 50, these anatomical forces may tend to flex tray component 30 along notch 50. For example, these anatomical forces may tend to flex rim 38 of tray component 30 along notch 50. When acting on a more rigid rim 38 without notch 50, these anatomical forces would be focused between tray component 30 and adhesive layer 44, especially along outer edge 42 of bone-contacting surface 34 of tray component 30. Thus, by providing notch 50 in tray component 30, the anatomical forces on outer edge 42 of bone-contacting surface 34 may be diminished to prevent tray component 30 from separating from tibia T.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A tibial prosthesis configured for securement to a patient's tibia and for articulation with an adjacent femoral component, the tibial prosthesis comprising:
   an articulating component having a concave articulating surface to facilitate articulation with the femoral component, wherein the articulating component is formed of a polymer; and
   a tray component having a proximal, receiving surface that receives the articulating component, a distal, bone-contacting surface opposite the receiving surface that is configured for securement to the patient's tibia, and an outer surface that extends proximally from the bone-contacting surface and beyond the receiving surface to define a rim for supporting the articulating component, the outer surface of the tray component defining a notch positioned to permit flexion of the rim relative to the bone-contacting surface of the tray component, wherein flexion of the rim relative to the bone-contacting surface is configured to reduce forces on an outer edge of the bone-contacting surface to inhibit the tray component from separating from the patient's tibia, wherein the rim comprises an inner surface that defines a peripheral boundary of the receiving surface, and wherein the entire receiving surface within the peripheral boundary is a planar surface.

2. The tibial prosthesis of claim 1, wherein at least a portion of the notch is located proximally of the receiving surface of the tray component.

3. The tibial prosthesis of claim 1, wherein at least a portion of the notch is located distally of the receiving surface of the tray component.

4. The tibial prosthesis of claim 1, wherein the notch is defined between a proximal chamfered portion of the outer surface and a distal chamfered portion of the outer surface, the proximal and distal chamfered portions of the outer surface intersecting at an inflection point, the rim of the tray component having a minimum thickness at the inflection point.

5. The tibial prosthesis of claim 1, wherein the rim includes a top end, at least a portion of the articulating component being located atop the top end of the rim.

6. The tibial prosthesis of claim 1, wherein the tray component includes a flange that projects inwardly from a top end of the rim toward the articulating component, the articulating component defining a groove that is positioned to receive the flange of the tray component.

7. The tibial prosthesis of claim 1, wherein the articulating component is coupled to the tray component by at least one of an interference fit, a mechanical fastener, and an adhesive.

8. The tibial prosthesis of claim 1, wherein the tray component is formed of a metal.

9. The tibial prosthesis of claim 1, wherein the notch extends around a circumference of the rim.

10. The tibial prosthesis of claim 1, wherein the tray component is stemless.

11. A tibial prosthesis configured for securement to a patient's tibia and for articulation with an adjacent femoral component, the tibial prosthesis comprising:
    an articulating component having a concave articulating surface to facilitate articulation with the femoral component, wherein the articulating component is formed of a polymer; and
    a tray component having a proximal, receiving surface that receives the articulating component and a distal, bone-contacting surface opposite the receiving surface that is configured for securement to the patient's tibia, the tray component including a rim that extends proximally beyond the receiving surface to support the articulating component, the rim defining a notch that extends into the rim until reaching an inflection point, the inflection point located along an arcuate surface of the rim to permit flexion of the rim relative to the bone-contacting surface of the tray component at the inflection point, wherein flexion of the rim relative to the bone-contacting surface is configured to reduce forces on an outer edge of the bone-contacting surface to inhibit the tray component from separating from the patient's tibia, wherein the rim comprises an inner surface that defines a peripheral boundary of the receiving surface, and wherein the entire receiving surface within the peripheral boundary is a planar surface.

12. The tibial prosthesis of claim 11, wherein the rim has an outer surface opposite the inner surface, the outer surface of the rim defining the notch.

13. The tibial prosthesis of claim 12, wherein the notch is defined between a proximal chamfered portion of the outer surface and a distal chamfered portion of the outer surface, the proximal and distal chamfered portions of the outer surface each defining an acute angle relative to a longitudinal axis of the patient's tibia.

14. The tibial prosthesis of claim 12, wherein the inner surface of the tray component includes a flange extending inwardly from the inner surface at a location above and opposite the notch.

15. The tibial prosthesis of claim 11, wherein the notch extends distally beneath the receiving surface of the tray component.

16. The tibial prosthesis of claim 11, wherein the outer edge of the bone-contacting surface defines an outer-most perimeter of the tray component.

17. The tibial prosthesis of claim 11, wherein the notch terminates distally upon reaching the outer edge of the bone-contacting surface.

18. The tibial prosthesis of claim 11, wherein the notch terminates proximally before reaching a top end of the rim, the rim extending proximally in a direction substantially perpendicular to the bone-contacting surface between the notch and the top end of the rim.

19. The tibial prosthesis of claim 11, wherein the notch extends substantially entirely around the tray component.

20. The tibial prosthesis of claim 11, wherein the rim has an outer surface opposite the inner surface, and wherein the rim of the tray component is a solid structure that is substantially devoid of openings between the outer surface and the inner surface of the rim.

21. The tibial prosthesis of claim 11, wherein the tray component is stemless.

* * * * *